United States Patent
Weser et al.

(10) Patent No.: US 10,322,079 B2
(45) Date of Patent: *Jun. 18, 2019

(54) HAIR DYE

(71) Applicant: Henkel AG & Co. KGaA, Duesseldorf (DE)

(72) Inventors: Gabriele Weser, Neuss (DE); Ulrike Schumacher, Duesseldorf (DE); Juergen Schoepgens, Schwalmtal (DE); Burkhard Mueller, Duesseldorf (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 1 day.

This patent is subject to a terminal disclaimer.

(21) Appl. No.: 15/826,689

(22) Filed: Nov. 30, 2017

(65) Prior Publication Data

US 2018/0168998 A1  Jun. 21, 2018

(30) Foreign Application Priority Data

Dec. 19, 2016 (DE) .................. 10 2016 225 375

(51) Int. Cl.
| | |
|---|---|
| *A61Q 5/10* | (2006.01) |
| *A61K 8/92* | (2006.01) |
| *A61K 8/34* | (2006.01) |
| *A61K 8/44* | (2006.01) |
| *A61K 8/73* | (2006.01) |
| *A61K 8/81* | (2006.01) |
| *A61K 8/41* | (2006.01) |
| *A61K 8/86* | (2006.01) |
| *A61K 8/19* | (2006.01) |

(52) U.S. Cl.
CPC ............. *A61K 8/922* (2013.01); *A61K 8/19* (2013.01); *A61K 8/345* (2013.01); *A61K 8/41* (2013.01); *A61K 8/415* (2013.01); *A61K 8/44* (2013.01); *A61K 8/73* (2013.01); *A61K 8/8147* (2013.01); *A61K 8/8152* (2013.01); *A61K 8/86* (2013.01); *A61Q 5/10* (2013.01); *A61K 2800/882* (2013.01)

(58) Field of Classification Search
CPC .......... A61Q 5/10; A61K 8/345; A61K 8/992; A61K 8/8152; A61K 8/73; A61K 8/41; A61K 8/415; A61K 8/86; A61K 2800/882
See application file for complete search history.

(56) References Cited

U.S. PATENT DOCUMENTS

| | | |
|---|---|---|
| 2009/0098074 A1 | 4/2009 | Barg et al. |
| 2010/0154135 A1 | 6/2010 | Matsunaga et al. |
| 2012/0285479 A1* | 11/2012 | Zirwen .................. A61K 8/046 132/208 |
| 2016/0008258 A1 | 1/2016 | Krause et al. |

OTHER PUBLICATIONS

Intellectual Property Office, Search Report under Section 17(5) for United Kingdom Patent Application No. GB1719900.1 dated Jan. 23, 2018.

* cited by examiner

*Primary Examiner* — Eisa B Elhilo

(74) *Attorney, Agent, or Firm* — Lorenz & Kopf, LLP

(57) ABSTRACT

The subject matter of the present disclosure relates to agents for oxidative hair dyeing, containing from about 78-about 95 wt. % water, oxidation dye precursor(s), alkalizing agents, from about 0.1-about 2 wt. % non-ionic tenside, from about 0.05-about 2 wt. % of a cross-linked copolymer from acrylic acid and non-ethoxylated esters of acrylic acid having linear C10-C30-monoalcohols, and xanthan gum, wherein only small quantities, if any, of linear saturated alkanols with two or three hydroxy groups and from 2 to 8 carbon atoms are contained in the alkyl group, also no saturated or unsaturated non-alkoxylated alkanols with a hydroxy group and from 1 to about 50 carbon atoms in the alk(en)yl group, no saturated or unsaturated alkanecarboxylic acids with from 1 to about 50 carbon atoms and no oxidants are included in the agent.

20 Claims, No Drawings

HAIR DYE

CROSS-REFERENCE TO RELATED APPLICATION

This application claims priority to German Patent Application No. 10 2016 225 375.1, filed Dec. 19, 2016, which is incorporated herein by reference in its entirety.

TECHNICAL FIELD

The present application relates to an oxidative hair dye, a kit, comprising said dye and a hair dyeing method by employing said hair dye.

BACKGROUND

To achieve permanent, intense colors with corresponding fastness properties, so-called oxidative dyes are used. Said dyes usually contain oxidative dye precursors, so-called developer components and coupler components. The developer components join together or couple with one or more coupler components to form, under the influence of oxidants or atmospheric oxygen, the actual dyes per se. Indeed, the oxidative dyes are exemplified by outstanding, long-lasting color results. To achieve natural-looking colors, however, a mixture from a larger number of oxidative dye precursors (ODP) must normally be used; in many cases, partially-oxidizing dyes are still used to create the tinting effect.

Most of the oxidative dyes used for stabilizing the dye precursors during storage and to accelerate the reaction during oxidative application have an alkali pH value, which is set with alkalizing agents such as alkanolamines, ammonia or inorganic bases.

To produce the dye, the alkali coloring component is usually mixed with a hydrous hydrogen peroxide solution to form a homogeneous creme or a homogeneous gel, and then applied immediately to the hair to be dyed. This dye mixture remains on the hair for a period of from about 5 to about 60 minutes, until the oxidative formation of the dye on the hair is complete. The dye mixture is then washed out.

The aforementioned oxidative precursors (OPC) and alkalizing agents are usually worked into the hair in a cosmetically suitable carrier, such as a creme, for example. The carrier guarantees a homogeneous distribution and an adequate dwell time of the hair dye on the hair.

The disadvantage is the complex manufacture of such a creme. The fusing of the fat components and the emulsification process requires a high amount of energy. The subsequent cooling process consumes large quantities of cooling water.

A further disadvantage is that a creme has to be packaged in a relatively complex manner. Due to their higher viscosity, cremes are incapable of flowing and cannot be transferred from a storage bottle into the application bottle, in which the hydrogen peroxide solution has already been placed, simply by tipping. Instead, the alkali dye cremes are packed primarily in flexible aluminum tubes, packaging material with high energy and raw material consumption.

A higher viscosity of the dye creme is a further disadvantage in terms of producing the application mixture. The alkali dye creme is mixed with the developer preparation by hand. The most homogeneous application mixture possible is required to achieve an effective color result. It must be possible to produce said mixture within the shortest possible time. This is because the oxidation dye precursors start to react as soon as they come into contact with the hydrogen peroxide and the atmospheric oxygen. The fastest possible mixture is achieved most readily if dye creme and developer preparation are as fluid as possible. Conversely, the application mixture itself should be more viscose so that it remains on the hair without dripping.

BRIEF SUMMARY

Agents for oxidative hair dyeing, kits-of-parts including the agents, and methods for oxidative hair dyeing using the agent are provided herein. In an embodiment, an agent for oxidative hair dyeing includes water, at least one oxidation dye precursor, at least one alkalizing agent, at least one non-ionic tenside, at least one cross-linked copolymer composed of acrylic acid and non-ethoxylated esters of acrylic acid with linear C10-C30 monoalcohols as monomers, xanthan gum, and optionally at least one linear, saturated alkanol with two or three hydroxy groups and from about 2 to about 8 carbon atoms in the alkyl group. Relative to the weight of the agent in each case, the agent includes the water in an amount of from about 78 to about 95 wt. %, the at least one non-ionic tenside in a total quantity of from about 0.1-about 3 wt. %, the at least one cross-linked copolymer present in a total quantity of from about 0.05 to about 2 wt. %, the xanthan gum present in a total quantity of from about 0.001-about 0.5 wt. %, and the at least one linear, saturated alkanol with two or three hydroxy groups and from about 2 to about 8 carbon atoms in the alkyl group in a total quantity of from 0-about 3 wt. %. No saturated or unsaturated non-alkoxylated alkanols with a hydroxy group and from about 1 to about 50 carbon atoms in the alk(en)yl group are included in the agent. No saturated or unsaturated alkanecarboxylic acids with from about 1 to about 50 carbon atoms are included in the agent. No oxidants are included in the agent.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

The present disclosure addressed the problem of providing an oxidative hair dye, which can be produced under the most cost-effective and sustainable conditions possible. The present disclosure also addressed the problem of providing an oxidative hair dye, which can be packaged under the most cost-effective and sustainable conditions possible. The present disclosure also addressed the problem of providing an oxidative hair dye, which is simple to blend and apply.

Said problems are solved by an agent for oxidative hair dye containing the following, in each case relative to its weight:
- from about 78-about 95 wt. %, preferably from about 83-about 91 wt. % water,
- at least one oxidation dye precursor,
- at least one alkalizing agent,
- at least one non-ionic tenside in a total quantity of from about 0.1-about 3 wt. %, preferably from about 0.3-about 2.5 wt. %, and more preferably from about 0.8-about 2 wt.-%,
- at least one cross-linked copolymer composed of acrylic acid and non-ethoxylated esters of acrylic acid with linear C10-C30 monoalcohols as monomers, wherein the cross-linked copolymer is present in a total quantity of 0.05 to 2 wt. %, from about 0.001-about 0.5 wt. %, preferably from about 0.01-about 0.3 wt. %, more preferably from about 0.05-about 0.1 wt. % xanthan gum, at least one linear, saturated alkanol with two or three hydroxy groups and from 2 to 8 carbon atoms in the alkyl group in a total quantity of from about 0-about 3 wt. %, wherein no saturated or unsaturated non-alkoxylated alkanols with a hydroxy group and from 1 to about 50 carbon atoms in the alk(en)yl group and no saturated or unsaturated alkanecarboxylic acids with from 1 to about 50 carbon atoms, and no oxidants are included in the agent The agent as contemplated herein constitutes the alkali dye component of an oxidative hair dye. This is usually mixed immediately before application with a hydrous hydrogen peroxide preparation and then applied to the hair to be dyed. Until mixed with the hydrous hydrogen peroxide preparation, the agent as contemplated herein contains no oxidants.

Water Content

The agent as contemplated herein contains, in each case relative to its weight, from about 78-about 95 wt. % water, preferably from about 83-about 91 wt. % water.

Alkalizing Agent

The agent as contemplated herein contains at least one alkalizing agent. The alkalizing agent preferred as contemplated herein for setting the preferred pH value is selected from the group comprising ammonium hydroxide, basic amino acids, alkali hydroxides, alkanolamines, alkali metal meta silicates, alkali phosphates and alkali hydrogen phosphates, as well as the mixtures thereof. Lithium, sodium and potassium, particularly sodium or potassium are preferred for use as alkali metal ions.

The basic amino acids that can be used as alkalizing agents are preferably selected from the group of L-arginine, D-arginine, D,L-arginine, L-lysine, D-lysine, D,L-lysine, L-arginine, D-arginine, D,L-arginine, are more preferably used as alkalizing agents as contemplated herein.

The alkali hydroxides that can be used as alkalizing agents are preferably selected from sodium hydroxide and potassium hydroxide.

The alkanolamines usable as alkalizing agents are preferably selected from primary amines with a $C_2$-$C_6$-alkyl base body having at least one hydroxyl group. More preferred alkanolamines are selected from the group comprising 2-aminoethan-1-ol (monoethanolamine), 3-aminopropan-1-ol, 4-amino-butan-1-ol, 5-aminopentan-1-ol, 1-aminopropan-2-ol, 1-aminobutan-2-ol, 1-aminopentan-2-ol, 1-aminopentan-3-ol, 1-aminopentan-4-ol, 3-amino-2-methylpropan-1-ol, 1-amino-2-methylpropan-2-ol, 3-aminopropan-1,2-diol, 2-amino-2-methylpropan-1,3-diol. Most preferred alkanolamines as contemplated herein are selected from the group of 2-aminoethan-1-ol, 2-amino-2-methylpropan-1-ol and 2-amino-2-methyl-propan-1,3-diol.

A most preferred alkalizing agent as contemplated herein is monoethanolamine (2-aminoethan-1-ol). To achieve the most odorless dye method possible and to optimize the color fastness properties of the dye, monoethanolamine is contained in a total quantity of from about 0.2-about 10 wt. %, preferably from about 0.5-about 8 wt. %, more preferably from about 1 to about 6 wt. % and most preferably from about 2 to about 4 wt. %-relative to the weight of the dye as contemplated herein.

In addition to and/or instead of monoethanolamine, other preferred dyes as contemplated herein are ammonium hydroxide, i.e. ammonia in the form of its hydrous solution. Suitable hydrous ammonia solutions are from about 10 to about 35 percentage solutions (calculated in vol. %.) 100 g of hydrous ammonia solution with 25 vol. % $NH_3$ contain approx. 50 g of ammonia. Ammonia is preferably used in the form of a from about 20 to about 30 vol. % solution, most preferably in the form of a 25 vol. % solution. In a most preferred embodiment, the dye as contemplated herein contains ammonium hydroxide in a quantity of from about 0.2 to about 6 wt. %, preferably from about 0.3 to about 5 wt. %, more preferably from about 0.5 to about 3 wt. % and most preferably from about 1 to about 2 wt. %, relative to the weight of the dye as contemplated herein.

Other alkalizing agents such as potassium hydroxide and sodium hydroxide can also be contained, preferably in a total quantity of from about 0.05 to about 1.5 wt. %, most preferably from about 0.1 to about 0.6 wt. %, in each case relative to the weight of the dye as contemplated herein.

In another most preferred embodiment, the dye as contemplated herein contains at least one alkalizing agent in a total quantity of from about 0.02-about 0.4 mol/100 g, preferably from about 0.05-about 0.3 mol/100 g, in each case in mol of alkalizing agents per 100 grams of agent as contemplated herein.

Preferred agents as contemplated herein are exemplified by a pH value in the range of from about 8-about 12, preferably from about 9-about 11.5, more preferably from about 9.5-about 10.5, in each case measured at 20° C.

Niotenside

The agent as contemplated herein contains, relative to its weight, at least one non-ionic tenside in a total quantity of from about 0.1-about 3 wt. %, preferably from about 0.3-about 2.5 wt. %, and most preferably from about 0.8-about 2 wt. %, in each case relative to the weight of said agent.

Tensides and emulsifiers according to the present disclosure are amphiphilic (bi-functional) compounds, which consist of at least one hydrophobic and at least one hydrophilic molecular part.

According to the present disclosure, saturated and unsaturated alkan-1-oles having at least 4 carbon atoms in the alk(en)yl radical, alkanecarboxylic acids having at least 4 carbon atoms in the alk(en)yl radical and glyceryl fatty acid mono and diesters having at least 4 carbon atoms in the fatty acid radical are not considered tensides.

The hydrophobic radical is preferably a hydrocarbon chain with from 8-about 30 carbon atoms, which can be saturated or unsaturated, linear or branched. This $C_8$-$C_{30}$ alkyl chain is most preferably linear. Basic properties of the tensides and emulsifiers are the oriented adsorption at boundary surfaces, as well as the aggregation to micelles and the formation of lyotrophic phases.

When selecting suitable tensides as contemplated herein, it may be preferable to use a mixture of tensides in order to set the properties of the oxidant dye as contemplated herein in an optimal manner.

Non-ionic tensides suitable for the agents as contemplated herein are all non-ionic tensides, suitable for use on the human body, which have at least one non-ionic group that renders them water-soluble, more particularly a polyethylene glycol ether group having at least 2 ethylene oxide units, a glycoside group, more particularly a glucose or methyl glucose group, a poly glycoside group with an average of more than one glycoside unit, one polyglycerine group having at least two glycerine units, one sorbitan group, one amid group or several different of said groups, for example a sorbitan group and a polyethylene glycol ether group, and one lipophilic alkyl group having from approximately 8 to 30 C-atoms, preferably from 10 to about 24 C-atoms. The non-ionic tensides most preferably used are selected from ethoxylated castor oil having from 7-about 80 mol of ethylene oxide per mol, ethoxylated $C_8$-$C_{30}$ alkanols having from 4-about 100 mol ethylene oxide per mol, ethoxylated $C_8$-$C_{30}$carbonic acid having from 5-about 30 mol of ethylene oxide per mol, having from 4-about 50 mol of ethylene oxide per mol of sorbitan monoesters of linear saturated and unsaturated $C_{12}$-$C_{30}$ carbonic acids, which can be hydroxylated, more particularly those from myristiric acid, palmitic acid, stearic acid of mixtures of said fatty acids, alkylmono- and oligoglycosides having from 8 to about 22 carbon atoms in the alkyl radical and the ethoxylated analogs thereof, as well as mixtures of the aforementioned substances.

Non-ionic tensides preferred as contemplated herein, which are selected from ethoxylated castor oil having from 7-about 80 ethylene oxide per mol, are selected from ethoxylated castor oil having from about 20-about 65 ethylene per mol, more preferably from ethoxylated castor oil having from about 30-about 60 ethylene per mol and most preferably ethoxylated castor oil having from about 40-about 55 ethylene mol ethylene oxide per mol.

The ethoxylated $C_8$-$C_{30}$ alkanols have the formula $R^1O(CH_2CH_2O)_nH$, wherein $R^1$ denotes a linear or branched alkyl and/or alkenyl radical having 8-30 carbon atoms and n, the average number of ethylene oxide units per molecule, for integers from 4-about 100, preferably from 6-about 30, more preferably from 12 to about 20 mol ethylene oxide to about 1 mol alkanol, which is preferably selected from capryl alcohol, 2-ethylhexyl alcohol, caprin alcohol, lauryl alcohol, isotridecyl alcohol, tridecyl alcohol, myristyl alcohol, cetyl alcohol, palmitoleyl alcohol, stearyl alcohol, isostearyl alcohol, oleyl alcohol, elaidyl alcohol, petroselinyl alcohol, arachyl alcohol, gadoleyl alcohol, behenyl alcohol, erucyl alcohol and brassidyl alcohol, as well as the technical mixtures thereof. Adducts from 10-about 100 mol ethylene oxide on technical fat alcohols having from 12-18 carbon atoms, such as for example coco, palm, palm kernel or sebum fat alcohols are also suitable. Trideceth-6, Isotrideceth-6, Undeceth-6, Myreth-6, Laureth-10, Laureth-12, Laureth-15, Laureth-20, Laureth-30, Myreth-10, Myreth-12, Myreth-15, Myreth-20, Myreth-30, Ceteth-10, Ceteth-12, Ceteth-15, Ceteth-20, Ceteth-30, Steareth-10, Steareth-12, Steareth-15, Steareth-20, Steareth-30, Oleth-10, Oleth-12, Oleth-15, Oleth-20, Oleth-30, Ceteareth-10, Ceteareth-15, Ceteareth-12, Ceteareth-15, Ceteareth-20, Ceteareth-30, as well as Coceth-10, Coceth-12, Coceth-15, Coceth-20 and Coceth-30 are more preferred; Ceteth-10, Ceteth-12, Ceteth-15, Ceteth-20, Ceteth-30, Steareth-10, Steareth-12, Steareth-15, Steareth-20 and Steareth-30, as well as the mixtures thereof, are most preferred.

The ethoxylated $C_8$-$C_{30}$ carbonic acids have the formula $R^1O(CH_2CH_2O)_nH$, wherein $R^1O$ denotes a linear or branched, saturated or unsaturated acyl radical having from 8-about 30 carbon atoms and n, the average number of ethylene oxide units per molecule, for integers from 5-about 30, preferably from 6-about 20, more preferably from 6 to 12 mol ethylene oxide to 1 mol $C_8$-$C_{30}$ carbonic acid, which is preferably selected from capryl alcohol, 2-ethylhexyl alcohol, caprin alcohol, lauric acid, isotridecaric acid, myristiric acid, cetyl acid, palmitoleic acid, stearic acid, isostearic acid, oleic acid, elaidic acid, petroselic acid, arachine acid, gadoleic acid, behenic acid, erucic acid and brassidic acid, as well as the technical mixtures thereof. Adducts from 5-about 30, preferably from 6-about 20, more preferably from 6 to 12 mol of ethylene oxide on technical fatty acids having from 12-18 carbon atoms, such as coco, palm, palm kernel or sebum fat alcohols are also suitable.

Agents particularly preferred as contemplated herein contain at least one non-ionic tenside in a total quantity of from about 0.3-about 2.5 wt. %, preferably from about 0.8-about 2 wt. %, relative to the weight of the agent in each case.

Agents particularly preferred as contemplated herein contain at least one non-ionic tenside, selected from ethoxylated castor oil having from about 7-about 80 mol ethylene oxide per mol, ethoxylated $C_8$-$C_{30}$-alkanols having from 4-about 100 mol ethylene oxide per mol, ethoxylated $C_8$-$C_{30}$-carboxylic acids having from 5-about 30 mol ethylene oxide per mol, having from 4-about 50 mol ethylene oxide per mol ethoxylated sorbitan monoesters of linear saturated and unsaturated $C_{12}$-$C_{30}$-carboxylic acids, which can be hydroxylated, alkylmono-and-oligoglycosides having from 8 to about 22 carbon atoms in the alkyl radical, as well as mixtures of the aforementioned substances, in a total quantity of from about 0.1-3 wt. %, preferably from about 0.3-about 2.5 wt. %, and more preferably from about 0.8-about 2 wt., in each case relative to the weight of the agent.

Agents most preferred as contemplated herein contain at least one non-ionic tenside, selected from ethoxylated castor oil having from 7-about 80 mol ethylene oxide per mol, preferably having from about 20-about 65 mol ethylene oxide per mol ethoxylated castor oil, more preferably from ethoxylated castor oil having from about 30-about 60 mol ethylene oxide per mol, most preferably from ethoxylated castor oil having from about 40-about 55 mol ethylene oxide per mol, as well as mixtures of the aforementioned substances, in a total quantity of from about 0.1-about 3 wt. %, preferably from about 0.3-about 2.5 wt. %, and most preferably from about 0.8-about 2 wt. %, in each case relative to the weight of the agent.

A further essential feature of the agents as contemplated herein is the content of at least one cross-linked copolymer, composed of acrylic acid and non-ethoxylated esters of acrylic acid with linear C10-C30-monoalcohols as monomers, wherein the cross-linked copolymer is present in a total quantity of from about 0.05-about 2 wt. %, preferably from about 0.1-about 1.5 wt. %, more preferably from about 0.3-about 1 wt. %, particularly from about 0.5-about 0.8 wt. %, relative to the weight of the agent in each case.

The at least one cross-linked copolymer from acrylic acid and non-ethoxylated esters of acrylic acid having linear C10-C30 mono-alcohols is preferably selected from copolymers having the INCI trade name of Acrylates/C10-30 Alkyl Acrylate Crosspolymer. Sucrose allyl ether or pentaerythrityl allyl ether is preferably contained as the cross-linking agent.

Cross-linked copolymers from acrylic acid and non-ethoxylated esters of acrylic acid having linear C10-C30 mono-alcohols, which are most preferred as contemplated herein, can be obtained by polymerizing a monomer mixture which—in each case relative to its weight—contains from about 80 to about 99 wt. %, preferably from about 90 to about 98 wt. %, acrylic acid, at least one non-ethoxylated ester of acrylic acid having linear C10-C30 mono-alcohols in a total quantity of from about 0.9-about 19.9 wt. %, preferably from about 2-about 10 wt. %, as well as a cross-linking agent in a total quantity of from about 0.1-about 4 wt. %.

Other cross-linked copolymers from acrylic acid and non-ethoxylated esters having linear C10-C30 mono-alcohols, which are most preferred as contemplated herein, are exemplified in that their 0.5 wt. % dispersion in water at 25° C. and a pH value in the range of from about 5.8-about 6.3 has a viscosity in the range of from about 45,000 to about 65,000 mPas, measured by employing a Brookfield RVF or a Brookfield RVT viscometer at a rotational frequency of 20 rpm with Spindle #7.

The content of the at least one cross-linked copolymer, constructed from acrylic acid and non-ethoxylated esters with acrylic acid having linear C10-C30 mono-alcohols as monomers, is preferably selected such that the viscosity of the agent as contemplated herein is within the range of from about 10-about 2000 mPas, preferably from about 200-about 1400 mPas, more preferably from about 500-about 1000 mPas, in each case measured at 20° C. by employing a Brookfield rotational viscometer at a rotational frequency of 20 rpm with Spindle 2.

A further essential feature of the agent as contemplated herein is the content of from about 0.001-about 0.5 wt. %, preferably from about 0.01-about 0.3 wt. %, more preferably from about 0.05-about 0.1 wt. % xanthan gum, in each case relative to the weight of the agent as contemplated herein.

The agents as contemplated herein and used as contemplated herein contain, in each case relative to their weight, at least one linear saturated alcohol having two or three hydroxy groups and from 2 to 8 carbon atoms in the alkyl group in a total quantity of from about 0-about 3 wt. %, preferably from about 0.1-about 2.2 wt. %. Particularly preferred linear saturated alkanols having two or three hydroxy groups and from 2 to 8 carbon atoms in the alkyl group are selected from 1,2-propandiol and glycerine, as well as mixtures thereof. Most preferred are from about 0-about 3 wt. %, preferably from about 0.1-about 2.2 wt. % 1,2-propandiol, in each case relative to the weight of the agent. At least one linear saturated alkanol having two or three hydroxy groups and from 2 to 8 carbon atoms in the alkyl group, including 1,2-propandiol is also preferably contained, in a total quantity of from about 0-about 3 wt. %, preferably from about 0.1-about 2.2 wt. %, in each case relative to the weight of the agent.

The agents as contemplated herein and used as contemplated herein do not contain any saturated or unsaturated non-alkoxylated alkanols having a hydroxy group and from 1 to about 50 carbon atoms in the alk(en)yl group; more particularly, the agents as contemplated herein contain no ethanol, no isopropanol, no linear fat alcohols such as cetyl- or stearyl alcohol, and no branched alkanols, such as 2-octyldodecanol.

Moreover, the agents as contemplated herein contain no saturated or unsaturated alkan carbonic acids having from 1 to about 50 carbon atoms, more particularly no oleic acids and no stearic acids or the salts thereof.

Agents preferred as contemplated herein and preferably used as contemplated herein are exemplified in that they contain, relative to the weight thereof, polyethylenglycol(s) having an average molecular weight of from about 100 to about 100,000 g·mol$^{-1}$ in a total quantity of from about 0-about 0.2 wt. %, preferably from about 0-about 0.1 wt. %. As contemplated herein, polyethylene glycols are compounds of the formula HO(CH$_2$CH$_2$O)$_n$H, wherein the index n denotes the degree of polymerization and is an integer from 3-about 2300.

It has emerged that saturated and unsaturated non-alkoxylated alkanols having a hydroxy group and from 1 to about 50 carbon atoms in the alk(en)yl group, more particularly ethanol and isopropanol, also linear saturated alkanols with two or three hydroxy groups and from 2 to 8 carbon atoms in the alkyl group and polyethylene glycols having an average molecular weight from about 100 to about 100,000 g·mol$^{-1}$ have a negative impact on the quality of the gel consistency, and therefore the total content thereof, as described above, should be limited and as low as possible.

Moreover, agents preferred as contemplated herein and preferably used as contemplated herein preferably contain fatty substances having a melting point of about 30° C. and above at 1013 mbar and a water-solubility of about 0.005 wt. % and below in a total quantity of from about 0-about 0.1 wt. %, preferably about 0 wt. %, relative to the weight of the agent. Said fatty substances include waxes, hardened oils and fats, as well as esters from fatty acids and fat alcohols having a melting point of about 30° C. and over at 1013 mbar.

Moreover, agents as contemplated herein and used as contemplated herein preferably contain at least one cationic polymer.

The cationic polymers can be homo- or copolymers or polymers based on natural polymers, wherein the quaternary nitrogen groups are contained either in the polymer chain or preferably as a substituent on one or more of the monomers. The ammonium group-containing monomers cannot be copolymerized with non-cationic monomers. Suitable cationic monomers are unsaturated, radically polymerizable compounds, which carry at least one cationic group, more particularly ammonium-substituted vinyl monomers, such as trialkylmethacryloxyalkylammonium, trialkylacryloxyalkylammonium, dialkyldiallylammonium and quaternary vinylammonium monomers having cyclical, cationic nitrogen containing groups, such as pyridinium, imidazolium or quaternary pyrrolidones, e.g. alkylvinylimidazolium, alkylvinylpyridinium, or alkylvinylpyrrolidone salts. The alkyl groups of said monomers are preferably low alkyl groups, such as to C7-alkyl groups, more preferably to C3-alkyl groups.

The ammonium group-containing monomers cannot be copolymerized with non-cationic monomers. Suitable comonomers include acrylamide, methacrylamide, alkyl and dialkylacrylamide, alkyl- and dialkylmethacrylamide, alkylacrylate, alkylmethacrylate, vinyl caprolactone, vinyl caprolactam, vinyl pyrrolidone, vinyl ester, e.g. vinyl acetate, vinyl alcohol, propylene glycol or ethylene glycol, wherein the alkyl groups of said monomers are preferably C1-to C7-alkyl groups, more preferablyC1-to C3-alkyl groups.

From the multitude of said polymers, the following have proven to be particularly effective constituents of the active ingredient combination as contemplated herein:

polymeric dimethyldiallyl ammonium salts and the copolymers thereof having esters and amides of acrylic acid and methacrylic acid. Particularly preferred polymers of this type are dimethyldiallyl ammonium chlorideacrylamid-copolymers, more particularly those having the INCI trade name Polyquaternium-7. Polyquaternium-7 is available as the commercial product Merquat® 550, for example. Another preferred polymer of this type is the homopolymer poly(dimethyldiallylammoniumchloride), more particularly the homopolymers having the INCI trade name Polyquaternium-6. Polyquaternium-6 is available as the commercial product Merquat® 100, for example. Other preferred polymers of this type are terpolymers from dimethyldiallyl ammonium chloride, acryl amide and ammonium acrylate, more particularly those having the INCI trade name Polyquaternium-39. Polyquaternium-39 is available as the commercial products Merquat® 3330 and Merquat® 3331, for example. Other preferred polymers of this type are copolymers from dimethyldiallyl ammonium chloride and acrylic acid, more particularly those having the INCI trade name Polyquaternium-22. Polyquaternium-22 is available as the commercial product Merquat® 280, for example.

Homopolymers of the general formula $-\{CH_2-[CR^1COO-(CH_2)_mN^+R^2R^3R^4]\}_n X^-$, wherein $R^1$ is $-H$ or $-CH_3$, $R^2$, $R^3$ and $R^4$ independently of one another are selected from C1-4-alkyl-, C1-4-alkenyl- or C1-4-hydroxy alkyl groups, m=1, 2, 3 or 4, n is a natural number and $X^-$ is a physiologically tolerated organic or inorganic anion. Of said polymers, those preferred as contemplated herein meet at least one of the following conditions: $R^1$ denotes a methyl group, $R^2$, $R^3$ and $R^4$ denote methyl groups, m has a value of 2. Physiologically-compatible counter-ions $X^-$ include halogenide ions, sulfate ions, phosphate ions, methosulfate ions, as well as organic ions such as lactate-, citric-, tartrate- and acetate ions. Methosulfates and halogenide ions, more particularly chloride, are preferred.

Other preferred suitable cationic polymers derived from synthetic polymers include copolymer from A1) from about 0.1 to about 50%, preferably from about 10 to about 50% (relative to the total number of monomers in the copolymer) monomers having the Formula (Ia)

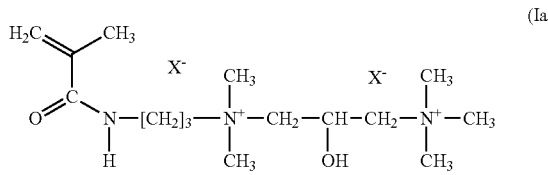

(Ia)

wherein X stands for chloride, sulfate, methosulfate and

A2) Monomers from the group of acrylic acid, methacrylic acid, as well as the alkali metal and ammonium salts of said acids, wherein the monomer A2 makes up from about 50 to about 99.9%, preferably makes up from about 50 to about 90% (relative to the total number of monomers in the copolymer) of the copolymer;

A most preferred polymer, constructed as illustrated above, is commercially available under the INCI trade name Polyquaternium-74.

A particularly suitable homopolymer is poly(methacryloyloxyethyltrimethylammonium-chloride), cross-linked if desired, having the INCI trade name Polyquaternium-37. Such products are commercially available under the trade names Rheocare® CTH (Cosmetic Rheologies) and Synthalen® CR (3V Sigma).

The homopolymer is preferably used in the form of an anhydrous polymer dispersion. Such polymer dispersions are commercially available under the trade names Salcare® SC 95 and Salcare® SC 96.

Suitable cationic polymers, which are derived from natural polymers, are cationic derivatives of polysaccharides, cationic derivatives of cellulose, starch or guar, for example. Chitosan and chitosan derivatives are also suitable. Cationic polysaccharides have the general formula

G is an anhydroglucose radical, for example starch or cellulose anhydroglucose;

B is a divalent compound group, or example alkylene, oxyalkylene, polyoxyalkylene or hydroxyalkylene;

$R_a$, $R_b$ and $R_c$ are, independently of one another, alkyl, aryl, alkylaryl, arylalkyl, alkoxyalkyl or alkoxyaryl, each having up to 18 carbon atoms, wherein the total number of carbon atoms in $R_a$, $R_b$ and $R_c$ is preferably a maximum of 20;

$A^-$ is a common counter-ion, preferably chloride.

Cationic, i.e. quaternized, celluloses are commercially available with various degrees of substitution, cationic charge density, nitrogen content and molecular weights. For example, Polyquaternium-67 is offered on the market under the trade names Polymer® SL or Polymer® SK (Amerchol). Another highly preferred cellulose is offered under the trade name Mirustyle® CP from Croda. This is a cellulose derivatized as trimonium and cocodimonium hydroxyethylcellulose having the INCI trade name Polyquaternium-72. Polyquaternium-72 can be used both in solid form and also pre-dissolved in a hydrous solution. Other cationic celluloses are available under the trade names Polymer JR® 400 (Amerchol, INCI trade name Polyquaternium-10), as well as Polymer Quatrisoft® LM-200 (Amerchol, INCI trade name Polyquaternium-24). Other commercial products are the compounds Celquat® H 100 and Celquat® L 200. Particularly preferred cationic celluloses are Polyquaternium-10, Polyquaternium-24, Polyquaternium-67 and Polyquaternium-72.

Suitable cationic guar derivatives are sold under the trade name Jaguar and have the INCI trade name Guar Hydroxypropyltrimonium Chloride. Moreover, particularly suitable cationic guar derivatives are commercially available also from Hercules under the trade name N-Hance. Other cationic guar derivatives are sold by BASF under the trade name Cosmedia®. A preferred cationic guar derivative is the commercial product AquaCat® from Hercules. This raw material is a pre-dissolved cationic guar derivative. The cationic guar derivatives are preferred as contemplated herein.

A suitable chitosan is sold by Kyowa Oil& Fat, Japan under the trade name Flonac®, for example. A preferred chitosan salt is chitosoniumpyrrolidoncarboxylate, which is sold under the trade name Kytamer® PC by Amerchol, USA, for example. Other chitosan derivatives are commercially under the trade names Hydagen® CMF, Hydagen® HCMF and Chitolam® NB/101.

Finally, sugar-based cationic polymers are also preferably used as contemplated herein. Such compounds include cationic alkyloligoglucosides, as shown in the figure below.

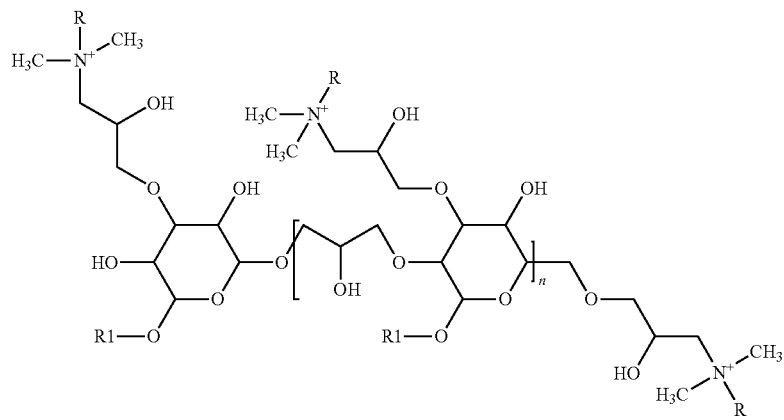

The formula above, the radicals R denote, independently of one another, a linear or branched C6 to C30 alkyl radical, a linear or branched C6-C30 alkenyl radical, the radical R preferably denotes a radical R selected from: Lauryl, myristyl, cetyl, stearyl, oleyl, behenyl or arachidyl. The radicals R1 denote, independently of one another, a linear or branched C6- to C30-alkyl radical, a linear or branched C6- to C30-alkenyl radical, the radical R preferably denotes a radical selected from butyl, capryl, caprylyl, octyl, nonyl, decanyl, lauryl, myristyl, cetyl, stearyl, oleyl, behenyl or arachidyl. The radicals R1 are more preferably identical. Even more preferably, the radicals R1 are selected from technical mixtures of fatty alcohol fragments of C6/C8 fat alcohols, C8/C10 fat alcohols, C10/C12 fat alcohols, C12/C14 fat alcohols, C12/C18 fat alcohols and most preferably, the technical fatty alcohol fragments are of plant origin. Particularly preferred examples of the cationic alkyloligoglucosides are the compounds having the INCI designations Polyquaternium-77, Polyquaternium-78, Polyquaternium-79, Polyquaternium-80, Polyquaternium-81 and Polyquaternium-82. Most preferred are the cation alkyloligoglucosides having the trade names Polyquaternium-77, Polyquaternium-81 and Polyquaternium-82. Such compounds can be obtained, for example, under the trade name of Poly Suga® Quat from Colonial Chemical Inc.

The cationic alkyloligoglucosides are preferably contained in a total quantity of from about 0.01 to about 6 wt. %, more preferably from about 0.05-about 4 wt. % and most preferably from about 0.1-about 3.5 wt. %, in each case relative to the weight of the agent as contemplated herein. The present disclosure also comprises the use, of course, of mixtures of cationic alkyloligoglucosides. In this case, it is preferable for a long-chained and a short-chained cationic alkyloligoglucoside to be contained at the same time.

A further cationic polymer can be obtained based on ethanolamine. The polymer is commercially available under the trade name Polyquaternium-71.

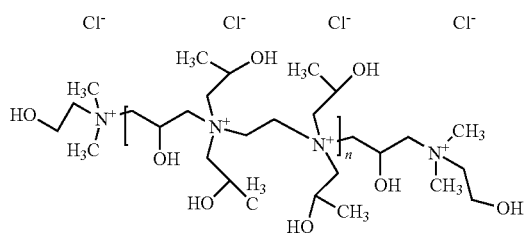

This polymer can be obtained, for example, under the trade name Cola® Moist 300 P from Colonial Chemical Inc.

Polyquaternium-71 is preferably contained in a quantity of from about 0.01-about 6 wt. %, preferably from about 0.05-about 4 wt. %, most preferably from about 0.1-about 3.5 wt. %, in each case relative to the weight of the agent as contemplated herein.

Other preferred cationic polymers include
cationized honey, the commercial product Honeyquat® 50, for example,
vinylpyrrolidone-vinylimidazoliummethochloride copolymers, such as those offered under the trade names Luviquat® FC 370, FC 550 and the INCI trade name Polyquaternium-16, as well as FC 905 and HM 552,
quaternized vinylpyrrolidone/dimethylaminoethylmethacrylate, e.g. vinylpyrrolidone/dimethylaminoethylmethacrylatmethosulfate copolymer, which is sold under the trade names Gafquat® 755 N and Gafquat® 734 by Gaf Co., USA and which has the INCI trade name Polyquaternium-11,
quaternated polyvinyl alcohol,
as well as the polymers known under the trade names Polyquaternium-2, Polyquaternium-17, Polyquaternium-18 and Polyquaternium-27, having quaternary nitrogen atoms in the polymer main chain,
vinylpyrrolidone-vinylcaprolactam-acrylat-terpolymers, as commercially available with acrylic acid esters and acrylic acid amides as a tertiary monomer unit under the trade name Aquaflex® SF 40, for example.

In a particularly preferred embodiment of the present disclosure, the agent as contemplated herein or the agent used as contemplated herein contains, in each case relative to the weight thereof, at least one cationic polymer in a total quantity of from about 0.01-about 6 wt. %, preferably from about 0.05-about 4 wt. %, more preferably from about 0.1-about 3.5 wt. %, most preferably from about 0.2-about 1 wt. %.

In another particularly preferred embodiment of the present disclosure, the agent as contemplated herein or used as contemplated herein contains, relative to the weight thereof, at least one cationic polymer, selected from dimethyldiallylammoniumchloride-acrylamide-copolymers, particularly those having the INCI trade name Polyquaternium-7, poly(dimethyldiallylammoniumchloride), terpolymers from dimethyldiallylammoniumchloride, acrylamide and ammonium acrylate, more particularly those having the INCI trade name Polyquaternium-39, as well as copolymers from dimethyldiallylammoniumchloride and acrylic acid, particularly those having the INCI trade name Polyquaternium-22, as well as the mixtures thereof, in a total quantity of from about 0.01-about 6 wt. %, preferably from about 0.05-about 4 wt. %, more preferably from about 0.1-about 3.5 wt. %, and most preferably from about 0.2-about 1 wt. %.

The agents preferred as contemplated herein are exemplified in that they contain sodium polyacrylate. As contemplated herein, sodium polyacrylate preferably comprises polymers with the CAS number 9003-04-7. Sodium polyacrylates preferred as contemplated herein have an average molecular weight $M_w$ in the range from about 1,000,000 to about 20,000,000 Dalton, preferably from about 6,000,000 to about 15,000,000 Dalton. The average molecular weight $M_w$ can, for example, be determined by employing gel permeation chromatography (GPC) with polystyrene as an internal standard according to DIN 55672-3, Version 8/2007.

The sodium polyacrylate leads to a further thickening of the agent, the agent taking on the consistency of a creamy gel at the same time.

Preferred agents as contemplated herein contain sodium polyacrylate in a total quantity of from about 0.1-about 1.5 wt. %, preferably from about 0.5-about 1.3 wt. %, particularly from about 0.8-about 1.1 wt. %, relative to the weight of the agent in each case.

In an especially preferred embodiment, the sodium polyacrylate is contained as a sodium polyacrylate pre-gelatinized in a water-in-oil emulsion. The sodium polyacrylate-containing water-in-oil emulsion preferably contains, in each case relative to its weight, from about 40-about 60 wt. % of sodium polyacrylate, from about 25-about 45 wt. % oil(s) in total, from about 0.5-about 4.9 wt. % tenside(s) in total and from about 0.5-about 4.9 wt. % water.

The oil contained in the sodium polyacrylate-containing water-in-oil emulsion is most preferably selected from natural and synthetic hydrocarbons, most preferably from mineral oil, paraffin oils, $C_{18}$-$C_{30}$ isoparaffins, particularly isoeicosane, polyisobutenes and polydecenes, $C_8$-$C_{16}$ isoparaffins, as well as 1,3-di-(2-ethylhexyl)-cyclohexane; the benzoic acid esters of linear or branched $C_{8-22}$ alkanols; triglycerides of linear or branched, saturated or unsaturated, where necessary hydroxylated $C_{8-30}$ fatty acids, particularly natural oils; the dicarboxylic acid esters of linear or branched $C_2$-$C_{10}$ alkanols; the esters of linear or branched saturated or unsaturated fat alcohols having from 2-about 30 carbon atoms with linear or branched saturated or unsaturated fatty acids having from 2-about 30 carbon atoms, which can be hydroxylated; the adducts of from 1 to 5 propylenoxide units of monovalent or multivalent $C_{8-22}$alkanols; the $C_8$-$C_{22}$ fatty alcohol esters of monovalent or multivalent $C_2$-$C_7$hydroxycarboxylic acids; the symmetrical, asymmetrical or cyclical esters of carbonic acids having $C_{3-22}$ alkanols, $C_{3-22}$ alkandiols or $C_{3-22}$ alkantriols; the esters of dimers of unsaturated $C_{12}$-$C_{22}$ fat alcohols (dimer fatty acids) having monovalent linear, branched or cyclical $C_2$-$C_{18}$ alkanols or having monovalent linear or branched $C_2$-$C_6$ alkanols; silicone oils, as well as mixtures of the aforementioned substances. The oil most preferred as contemplated herein is mineral oil.

The tenside contained in the sodium polyacrylate-containing water-in-oil emulsion is most preferably from non-ionic tensides. The non-ionic tensides most preferably used are selected from, having from about 7-about 80 mol of ethylene oxide per mol, ethoxylated castor oil, ethoxylated $C_8$-$C_{24}$ alkanols having from 5-about 30 mol ethylene oxide per mol, ethoxylated $C_8$-$C_{24}$carbonic acid having from 5-about 30 mol of ethylene oxide per mol, having from 4-about 50 mol of ethylene oxide per mol of sorbitan monoesters of linear saturated and unsaturated $C_{12}$-$C_{30}$ carbonic acids, which can be hydroxylated, more particularly those from myristiric acid, palmitic acid, stearic acid of mixtures of said fatty acids, alkylmono and oligoglycosides having from 8 to about 22 carbon atoms in the alkyl radical and the ethoxylated analogs thereof, as well as mixtures of the aforementioned substances.

The ethoxylated $C_8$-$C_{24}$ alkanols have the formula $R^1O(CH_2CH_2O)_nH$, wherein $R^1$ denotes a linear or branched alkyl and/or alkenyl radical having from 8-about 24 carbon atoms and n, the average number of ethylene oxide units per molecule, for integers from 5-about 30, preferably from 6-about 20, more preferably from 6 to 12 mol ethylene oxide to 1 mol alkanol, which is preferably selected from capryl alcohol, 2-ethylhexyl alcohol, caprin alcohol, lauryl alcohol, isotridecyl alcohol, tridecyl alcohol, myristyl alcohol, cetyl alcohol, palmitoleyl alcohol, stearyl alcohol, isostearyl alcohol, oleyl alcohol, elaidyl alcohol, petroselinyl alcohol, arachyl alcohol, gadoleyl alcohol, behenyl alcohol, erucyl alcohol and brassidyl alcohol, as well as the technical mixtures thereof. Adducts from 10-about 100 mol ethylene oxide on technical fat alcohols having 12-18 carbon atoms, such as for example coco, palm, palm kernel or sebum fat alcohols are also suitable. Trideceth-6, Isotrideceth-6, Undeceth-6, Myreth-6, Laureth-10, Laureth-12, Laureth-15, Laureth-20, Laureth-30, Myreth-10, Myreth-12, Myreth-15, Myreth-20, Myreth-30, Ceteth-10, Ceteth-12, Ceteth-15, Ceteth-20, Ceteth-30, Steareth-10, Steareth-12, Steareth-15, Steareth-20, Steareth-30, Oleth-10, Oleth-12, Oleth-15, Oleth-20, Oleth-30, Ceteareth-10, Ceteareth-15, Ceteareth-12, Ceteareth-15, Ceteareth-20, Ceteareth-30, as well as Coceth-10, Coceth-12, Coceth-15, Coceth-20 and Coceth-30 are more preferred; Trideceth-6 and Isotrideceth-6, as well as the mixtures thereof, are most preferred.

The ethoxylated $C_8$-$C_{30}$ carbonic acids have the formula $R^1O(CH_2CH_2O)_nH$, wherein $R^1O$ denotes a linear or branched, saturated or unsaturated acyl radical having from 8-about 30 carbon atoms and n, the average number of ethylene oxide units per molecule, for integers from 5-about 30, preferably from 6-about 20, more preferably from 6 to 12 mol ethylene oxide to 1 mol $C_8$-$C_{30}$ carbonic acid, which is preferably selected from capryl alcohol, 2-ethylhexyl alcohol, caprin alcohol, lauric acid, isotridecaric acid, myristiric acid, cetyl acid, palmitoleic acid, stearic acid, isostearic acid, oleic acid, elaidic acid, petroselic acid, arachine acid, gadoleic acid, behenic acid, erucic acid and brassidic acid, as well as the technical mixtures thereof. Adducts from 5-about 30, preferably from 6-about 20, more preferably 6 to 12 mol of ethylene oxide on technical fatty acids having from 12-18 carbon atoms, such as coco, palm, palm kernel or sebum fat alcohols are also suitable.

Agents most preferred as contemplated herein are exemplified in that they contain at least one sodium polyacrylate having an average molecular weight $M_w$ in the range from about 1,000,000 to about 20,000,000 Dalton, preferably from about 6,000,000 to about 15,000,000 Dalton, in a total quantity of from about 0.1-about 1.5 wt. %, preferably from about 0.5-about 1.3 wt. %, more preferably from about 0.8-about 1.1 wt. %, in each case relative to the total weight of the agent, wherein the sodium polyacrylate is contained pregelled in a water-in-oil emulsion, wherein said water-in-oil emulsion, in each case relative to its weight, contains from about 40-about 60 wt. % sodium polyacrylate, from about 25-about 45 wt. % oil(s) in total, preferably mineral oil, from about 0.5-about 4.9 wt. % tenside(s) in total, preferably from about 0.5-about 4.9 wt. % niotenside(s), and from about 0.5-about 4.9 wt. % water.

Agents as contemplated herein, which contain sodium polyacrylate, have a viscosity in the range of from about 10,000-about 75,000 mPas, preferably from about 12,000-about 60,000 mPas, more preferably from about 13,000-about 50,000 mPas, most preferably from about 15,000-about 25,000 mPas, in each case measured at 20° C. by employing a Brookfield rotational viscometer at a rotational frequency of 4 rpm with Spindle 5.

Agents preferred as contemplated herein and preferably used as contemplated herein contain, in each case relative to their weight, at least one oil in a total quantity of from about 0.1 to about 2 wt. %, preferably from about 0.2-about 1.5 wt. %, most preferably from about 0.5-about 1 wt. %. In another preferred embodiment, agents as contemplated herein and used as contemplated herein are free of oils.

A further essential feature of the agent as contemplated herein is the content of at least one oxidation dye precursor.

On the basis of their reaction behavior, oxidative dye precursors can be divided into two categories, so-called developer components and coupler components.

During the oxidative dyeing process, coupler components do not achieve any significant coloration by themselves. They always require the presence of developer components. Developer components can combine together to form the actual dye.

The developer and coupler components are normally used in a free form. In the case of substances with amino groups, however, use of the salt form thereof, more particularly in the form of hydrochlorides and hydrobromides or sulfates, may be preferred. Oxidation dye precursors include oxidation dye precursors of the developer and coupler types. Particularly suitable oxidation dye precursors of the developer type are selected from at least one compound from the group including of p-phenylenediamine, p-toluylenediamine, 2-(2-hydroxyethyl)-p-phenylenediamine, 2-(1,2-dihydroxyethyl)-p-phenylenediamine, N, N-bis (2-hydroxyethyl)-p-phenylenediamine, 2-methoxymethyl-p-phenylenediamine, N-(4-amino-3-methylphenyl)-N-[3-(1H-imidazol-1-yl) propyl] amine, N, N'-bis (2-hydroxyethyl)-N, N'-bis-(4-aminophenyl)-1,3-diamino-propane-2-ol, bis-(2-hydroxy-5-aminophenyl) methane, 1,3-bis (2,5-diaminophenoxy) propan-2-ol, N, N'-bis (4-aminophenyl)-1,4-diazacycloheptane, 1, 10-bis (2,5-diaminophenyl)-1,4,7,10-tetraoxadecane, p-aminophenol, 4-amino-3-methylphenol, 4-amino-2-aminomethylphenol, 4-amino-2-(1,2-dihydroxyethyl) phenol, 4-amino-2-(diethylaminomethyl) phenol, 4,5-diamino-1-(2-hydroxyethyl)pyrazole, 2,4,5,6-tetraaminopyrimidine, 4-hydroxy-2, 5,6-triaminopyrimidine, 2-hydroxy-4,5,6-triaminopyrimidine, 2,3-diamino-6,7-dihydro-1H, 5H-pyrazolo [1,2-a] pyrazol-1-one and the physiologically tolerated salts thereof. Most preferred developer components are selected from p-toluylendiamine, 2-(2-hydroxyethyl)-p-phenylendiamine, N,N-bis-(2-hydroxyethyl)-p-phenylendiamine, 2-methoxymethyl-p-phenylendiamine and/or 4,5-diamino-1-(2-hydroxyethyl)-pyrazol and the physiologically tolerated salts and mixtures thereof.

Particularly suitable oxidation dye precursors of the coupler type are selected from the group including of 3-aminophenol, 5-amino-2-methylphenol, 3-amino-2-chlor-6-methylphenol, 2-hydroxy-4-aminophenoxyethanol, 5-amino-4-chlor-2-methylphenol, 5-(2-hydroxyethyl)-amino-2-methylphenol, 2,4-dichlor-3-aminophenol, 2-aminophenol, 3-phenylendiamine, 2-(2,4-diaminophenoxy)ethanol, 1,3-bis(2,4-diaminophenoxy)propane, 1-methoxy-2-amino-4-(2-hydroxyethylamino)benzol (2-amino-4-[(2-hydroxyethyl)amino]-anisol), 1,3-bis(2,4-diaminophenyl)propane, 2,6-bis(2'-hydroxyethylamino)-1-methylbenzol, 2-({3-[(2-hydroxyethyl)amino]-4-methoxy-5-methylphenyl}amino) ethanol, 2-({3-[(2-hydroxyethyl)amino]-2-methoxy-5-methylphenyl} amino)ethanol, 2-({3-[(2-hydroxyethyl) amino]-4,5-dimethylphenyl}amino)ethanol, 2-[3-morpholin-4-ylphenyl)amino] ethanol, 3-amino-4-(2-methoxyethoxy)-5-methylphenylamine, 1-amino-3-bis-(2-hydroxyethyl) aminobenzol, resorcin, 2-methylresorcin, 4-chlorresorcin, 1,2,4-trihydroxybenzol, 2-amino-3-hydroxypyridin, 3-amino-2-methylamino-6-methoxypyridin, 2,6-dihydroxy-3,4-dimethylpyridin, 3,5-diamino-2,6-dimethoxypyridin, 1-phenyl-3-methylpyrazol-5-on, 1-naphthol, 1,5-dihydroxynaphthalin, 2,7-dihydroxynaphthalin, 1,7-dihydroxynaphthalin, 1,8-dihydroxynaphthalin, 4-hydroxyindol, 6-hydroxyindol, 7-hydroxyindol, 4-hydroxyindolin, 6-hydroxyindolin, 7-hydroxyindolin or mixtures of said compounds or the physiologically compatible salts thereof. Most preferred coupler components are selected from 3-aminophenol, 5-amino-2-methylphenol, 3-amino-2-chlor-6-methylphenol, 2-hydroxy-4-aminophenoxyethanol, 2-(2, 4-diaminophenoxy)ethanol, 1-methoxy-2-amino-4-(2-hydroxyethylamino)benzol (2-Amino-4-[(2-hydroxyethyl) amino]-anisol), resorcin, 2-methylresorcin, 4-chlorresorcin, 2-amino-3-hydroxypyridin, as well as the physiologically compatible salts and mixtures thereof.

In a preferred embodiment, the dyes as contemplated herein contain one or more oxidation dye precursors in a total quantity from about 0.001 to about 5.0 wt. %, preferably from about 0.01 to about 4.0 wt. %, more preferably from about 0.2 to about 3.5 wt. %, even more preferably from about 0.3 to about 2.5 wt. % and most preferably from about 0.7 to about 1.8 wt. %, relative to the weight of the dye as contemplated herein and/or the weight of the composition used as contemplated herein (M1).

In a preferred embodiment, the dyes as contemplated herein contain one or more oxidation dye precursors, selected from at least one developer component and optionally at least one coupler component, in a total quantity from about 0.001 to about 5.0 wt. %, preferably from about 0.01 to about 4.0 wt. %, more preferably from about 0.2 to about 3.5 wt. %, even more preferably from about 0.3 to about 2.5 wt. % and most preferably from about 0.7 to about 1.8 wt. %, relative to the weight of the dye as contemplated herein and/or the weight of the composition used as contemplated herein (M1).

In a more preferred embodiment of the present disclosure, the agent as contemplated herein contains at least one partially-oxidizing dye. In oxidative hair dyes, partially-oxidizing dyes often serve to tint unwanted red undertones, which can be produced by the melanin decomposition products, or to tint certain blond tones. In order to obtain a balanced and subtle tint formation, the present disclosure may specify that the cosmetic agents with ODP additionally contain at least one partially-oxidizing dye.

Partially-oxidizing dyes are dyes that coat the substrate itself and do not require an oxidative process to create the color. Partially-oxidizing dyes are usually nitro-phenylendiamines, nitroaminophenols, azo dyes, anthraquinones or indophenols.

Partially-oxidizing dyes can be sub-divided into anionic, cationic and non-ionic partially-oxidizing dyes.

Preferred anionic partially-oxidizing dyes are the compounds known under the designations Acid Yellow 1, Yellow 10, Acid Yellow 23, Acid Yellow 36, Acid Orange 7, Acid Red 33, Acid Red 52, Pigment Red 57:1, Acid Blue 7, Acid Green 50, Acid Violet 43, Acid Black 1, Acid Black 52 and tetrabromophenol blue.

Preferred cationic partially-oxidizing dyes are cationic triphenylmethane dyes, such as Basic Blue 7, Basic Blue 26, Basic Violet 2 and Basic Violet 14, as well as aromatic systems, which are substituted with a quaternary nitrogen group, such as Basic Yellow 57, Basic Red 76, Basic Blue 99, Basic Brown 16 and Basic Brown 17 and HC Blue 16, as well as Basic Yellow 87, Basic Orange 31 and Basic Red 51.

Preferred non-ionic direct dyes are HC Yellow 2, HC Yellow 4, HC Yellow 5, HC Yellow 6, HC Yellow 12, HC Orange 1, Disperse Orange 3, HC Red 1, HC Red 3, HC Red 10, HC Red 11, HC Red 13, HC Red BN, HC Blue 2, HC Blue 11, HC Blue 12, Disperse Blue 3, HC Violet 1, Disperse Violet 1, Disperse Violet 4, Disperse Black 9, as well as 1,4-diamino-2-nitrobenzol, 2-amino-4-nitrophenol, 1,4-bis-(2-hydroxyethyl)amino-2-nitrobenzol, 3-nitro-4-(2-hydroxyethyl)aminophenol, 2-(2-hydroxyethyl)amino-4,6-dinitrophenol, 4-[(2-hydroxyethyl)amino]-3-nitro-1-methyl-benzol, 1-amino-4-(2-hydroxyethyl)amino-5-chlor-2-nitrobenzol, 4-amino-3-nitrophenol, 1-(2'-Ureidoethyl) amino-4-nitrobenzol, 2-[(4-amino-2-nitrophenyl)amino] benzoic acid, 6-nitro-1,2,3,4-tetrahydroquinoxalin, 2-hydroxy-1,4-naphthoquinone, picramic acid and the salts thereof, 2-amino-6-chloro-4-nitrophenol, 4-ethylamino-3-nitrobenzoic acid and 2-chlor-6-ethylamino-4-nitrophenol.

Moreover, partially-oxidizing dyes that occur in nature, such as Henna red, Henna neutral, Henna black, chamomile blossoms sandalwood, black tea, walnut, Cascara bark, sage, logwood, madder root, *catechu* and alkanna root, can also be used.

The cosmetic agent according preferably contains at least one partially-oxidizing agent in a total quantity of from about 0.001 to about 10 wt. %, preferably from about 0.01 to about 8 wt. %, more preferably from about 0.1 to about 5 wt. %, most preferably from about 0.5 to about 2 wt. %, relative to the total weight of the cosmetic agent and/or of the composition used as contemplated herein (M1).

Therefore, a further subject of the present disclosure is a kit-of-parts, comprising—packaged separately from one another:
a) at least one container (C1), containing an agent for oxidative hair dyeing containing the following, in each case relative to its weight:
from about 78-about 95 wt. %, preferably from about 83-about 91 wt. % water,
at least one oxidation dye precursor,
at least one alkalizing agent,
at least one non-ionic tenside in a total quantity of from about 0.1-about 3 wt. %, preferably from about 0.3-about 2.5 wt. %, and more preferably from about 0.8-about 2 wt.-%,
at least one cross-linked copolymer composed of acrylic acid and non-ethoxylated esters of acrylic acid with linear C10-C30 monoalcohols as monomers, wherein the cross-linked copolymer is present in a total quantity of from about 0.05 to about 2 wt. %,
from about 0.001-about 0.5 wt. %, preferably from about 0.01-about 0.3 wt. %, more preferably from about 0.05-about 0.1 wt. % xanthan gum,
at least one linear, saturated alkanol with two or three hydroxy groups and from 2 to 8 carbon atoms in the alkyl group in a total quantity of from about 0-about 3 wt. %,
wherein
no saturated or unsaturated non-alkoxylated alkanols with a hydroxy group and from 1 to about 50 carbon atoms in the alk(en)yl group and
no saturated or unsaturated alkanecarboxylic acids with from 1 to about 50 carbon atoms, and
no oxidants
are included in the agent,
and
b) at least one container (C2), containing an oxidant preparation (M2), which contains from about 40-about 96 wt. %, preferably from about 70-about 93 wt. %, more preferably from about 80-about 90 wt. % of water, also hydrogen peroxide in a total quantity of from about 0.5 to about 23 wt. %, preferably from about 2.5 to about 21 wt. %, more preferably from about 4 to about 20 wt. %, even more preferably from about 5 to about 18 wt. % and most preferably from about 6 to about 12 wt. %, and which has a pH value in the range from about 2.0 to about 6.5, preferably from about 2.5-about 5.5, more preferably from about 2.8 to about 5.0, in each case measured at 20° C., wherein each of the wt. % values are relative to the weight of the oxidant preparation (M2).

A further subject matter of the present disclosure is a method for oxidative hair dyeing comprising the following method steps:
i) Providing a cosmetic agent (M1) for the oxidative hair dyeing of keratinic fibers, containing
from about 78-about 95 wt. %, preferably from about 83-about 91 wt. % water,
at least one oxidation dye precursor,
at least one alkalizing agent,
at least one non-ionic tenside in a total quantity of from about 0.1-about 3 wt. %, preferably from about 0.3-about 2.5 wt. %, and more preferably from about 0.8-about 2 wt.-%,
at least one cross-linked copolymer composed of acrylic acid and non-ethoxylated esters of acrylic acid with linear C10-C30 monoalcohols as monomers, wherein the cross-linked copolymer is present in a total quantity of from about 0.05 to about 2 wt. %,
from about 0.001-about 0.5 wt. %, preferably from about 0.01-about 0.3 wt. %, more preferably from about 0.05-about 0.1 wt. % xanthan gum,
at least one linear, saturated alkanol with two or three hydroxy groups and from 2 to 8 carbon atoms in the alkyl group in a total quantity of from about 0-about 3 wt. %,
wherein
no saturated or unsaturated non-alkoxylated alkanols with a hydroxy group and from 1 to about 50 carbon atoms in the alk(en)yl group and
no saturated or unsaturated alkanecarboxylic acids with 1 to 50 carbon atoms, and
no oxidants
are included in the agent,
ii) Providing at least one oxidant preparation (M2), which contains from about 40-about 96 wt. %, preferably from about 70-about 93 wt. %, more preferably from about 80-about 90 wt. % of water, also hydrogen peroxide in a total quantity of from about 0.5 to about 23 wt. %, preferably from about 2.5 to about 21 wt. %, more preferably from about 4 to about 20 wt. %, even more preferably from about 5 to about 18 wt. % and most preferably from about 6 to about 12 wt. %, and which has a pH value in the range from about 2.0 to about 6.5, preferably from about 2.5-about 5.5, more preferably from about 2.8 to about 5.0, in each case measured at 20° C., wherein each of the wt. % values are relative to the weight of the oxidant preparation (M2), wherein at least one cation tenside is optionally contained, iii) Mixing the cosmetic agent (M1) with the oxidant preparation (M2), preferably in a weight ratio (M1):(M2) in the range from about 1:0.8 to about 1:2.5, preferably from about 1:1 to about 1:2, immediately afterwards
iv) Applying the mixture obtained in Step iii) onto the hair and leaving said mixture for a period of from about 1 to about 60 minutes, preferably from about 20 to about 45 minutes at room temperature and/or at from about 30-about 60° C., preferably at from about 32-about 50° C. on the hair,
v) Rinsing the hair with water and/or a cleansing composition, and
vi) where necessary, applying a post-treatment agent onto the hair and, where necessary, rinsing out, then drying.

For oxidative hair dyeing, immediately before the application on the hair, the one or more oxidation dye precursors and, where applicable, one or more partially-oxidizing dyes, are usually mixed with a hydrous oxidant-containing composition (M2) to produce the ready-to-use dye and then applied to the hair. In most cases, the agent as contemplated herein (M1) and the oxidant-containing composition (M2) are matched with one another such that, at a mixing ratio of 1 to 1, relative to the parts by weight, the ready-to-use application mixture has an initial concentration of hydrogen peroxide of from about 0.5-about 12 wt. %, preferably from about 2-about 10 wt. %, more preferably from about 3-about 6 wt. % of hydrogen peroxide (calculated as 100% $H_2O_2$), in each case relative to the weight of the application mixture. However, it is equally possible for the agent as contemplated herein (M1) and the oxidant-containing composition (M2) to be matched to one another such that the concentrations required in the ready-to-use oxidant dye (application mixture) is achieved through mixture ratios other than 1:1, for example through a weight-based mixture ratio of 1:2 or 1:3 or even 2:3.

Weight-based mixture ratios preferred as contemplated herein (M1):(M2) are within the range from about 1:0.8 to about 1:2.5, more preferably within the range of from about 1:1 to about 1:2.

As contemplated herein, the expression "room temperature" describes the temperature inside the room in which a person would usually use a hair dye, i.e. usually a bathroom or a hairdressing salon, in which a temperature within the range of from about 10-about 29° C. prevails.

The leaving of the hair dyeing application mixture in method step iv) in the hair dyeing method as contemplated herein or preferred as contemplated herein can also occur at a minimum of about 30° C., preferably at from about 30-about 60° C., more preferably at from about 32-about 50° C., if the hair is heated by employing a heating hood or a heat radiator, for example.

The oxidant preparation (M2) used in the dye kit as contemplated herein and preferred as contemplated herein, as well as in the dyeing method as contemplated herein and preferred as contemplated herein contains, in each case relative to the weight thereof, from about 40-about 96 wt. %, preferably from about 70-about 93 wt. %, most preferably from about 80-about 90 wt. % of water.

The oxidant preparation (M2) used in the dye kit as contemplated herein and preferred as contemplated herein, as well as in the dyeing method as contemplated herein and preferred as contemplated herein contains, in each case relative to the weight thereof, from about 0.5 to about 23 wt. %, preferably from about 2.5 to about 21 wt. %, more preferably from about 4 to about 20 wt. %, even more preferably from about 5 to about 18 wt. % and most preferably from about 6 to about 12 wt. % of hydrogen peroxide.

To stabilize the hydrogen peroxide, the oxidant preparation (M2) has a pH value in the range from about 2.0 to about 6.5, preferably from about 2.5-about 5.5, most preferably from about 2.8 to about 5.0, in each case measured at 20° C.

Cation Tenside in the Oxidant Preparation (M2)

The average viscosity of agents (M1) preferred as contemplated herein is in the range of from about 10-about 2000 mPas, preferably from about 200-about 1400 mPas, more preferably from about 500-about 1000 mPas, measured at 20° C. in each case, is excellently suited to the handling of this agent itself (production, placing in plastic bottles, metering for production of the mixture with the oxidant preparation). The oxidant preparation (M2) usually has a low viscosity in the range of from about 10-about 6000 mPas, preferably from about 200-about 5000 mPas, more preferably from about 1000-about 4500 mPas, in each case measured at 20° C. For application on the hair, however, the application mixture ought to have a substantially higher viscosity so that it remains on the hair for the entire exposure time (in the range of from about 5-about 60 minutes, preferably from about 30-about 45 minutes) without dripping. A distinction is drawn here as to whether the application mixture is produced by shaking the two compositions (M1) and (M2) in an application bottle, from which the application mixture is applied to the hair immediately after mixing by employing an application nozzle in the form of a bottle attachment (bottle application), or whether the application mixture is produced by stirring the two compositions (M1) and (M2) in a bowl, from which the application is mixture is applied to the hair immediately after mixing by employing a brush (brush application). The bottle application is particularly suitable for dyes that are sold in retail outlets trade with an application recommendation by the consumer itself. The brush application is particularly suitable for dyes that are produced in the hairdressing salon and applied to the consumer's hair by the hairdresser.

It has unexpectedly emerged that an application mixture having a viscosity particularly suitable for brush application is obtained if the agent as contemplated herein or preferred as contemplated herein (M1) is mixed with an oxidant preparation (M2) containing at least one cation tenside. During mixing, the interaction between the at least one cross-linked copolymer of acrylic acid and non-ethoxylated esters of acrylic acid with linear C10-C30 monoalcohols and the at least one cationic surfactant leads to the desired increase in viscosity. The pasty consistency of the application mixture thus obtained leads to optimum application properties, more particularly for the brush application. The application mixtures thus achieved, preferably with weight-based mixture ratios (M1):(M2) in the range of from about 1:0.8 to about 1:2.5 preferably have a viscosity in the range of from about 10000-about 100000 mPas, more preferably from about 12000-about 80000 mPas, most preferably from about 15000-about 40000 mPas, in each case measured at 20° C. (Brookfield viscometer, at a rotational frequency of 4 rpm with Spindle No. 5).

In a more preferred embodiment of the present disclosure, the oxidant preparation used as contemplated herein (M2) contains at least one cation tenside, preferably in a total quantity of from about 0.05-about 3 wt. %, more preferably from about 0.1-about 1.5 wt. %, most preferably from about 0.3-about 0.9 wt. %, in each case relative to the weight of the oxidant preparation (M2).

Cationic tensides are tensides, i.e. surfactant compounds, each having one or more positive charges. Cationic tensides contain exclusively positive charges. Usually, said tensides are constructed from a hydrophobic part and a hydrophilic head group, wherein the hydrophobic part normally of a hydrocarbon structure (e.g. including of one or two linear or branched alkyl chains), and the positive charge(s) are localized in the hydrophilic head group. Cationic tensides adsorb at boundary surfaces and aggregate in hydrous solutions above the critical micelle formation concentration to form positively charged micelles.

As contemplated herein, preferred cationic tensides are of the type of quaternary ammonium compounds, eterquats and alkyl amidoamines. Preferred quaternary ammonium compounds are ammonium halogenides, such as alkyltrimethyl-ammoniumchloride, dialkyldimethylammoniumchloride, trialkylmethylammoniumchloride, as well as the imidazolium compounds known under the INCI trade names of Quaternium-27 and Quaternium-83. Other preferred quaternary ammonium compounds are tetra alkyl ammonium salts, such as that known under the INCI trade name of Quaternium-52, a poly(oxy-1,2-ethanediyl), ((octadecylnitrilio)tri-2,1-ethanediyl)tris(hydroxy)-phosphate (1:1)-salt, which has the general structural formula (III), wherein x+y+z=10 are

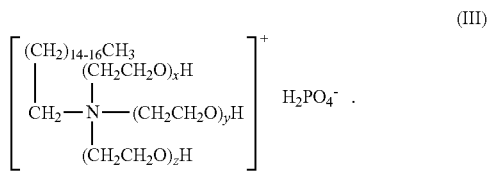

The long alkyl chains of the aforementioned tensides preferably have from 10 to about 22, more preferably from 12 to 18 carbon atoms. Particularly preferred are behenyl trimethyl ammonium chloride, stearyl trimethyl ammonium chloride and cetyl trimethyl ammonium chloride, wherein stearyl trimethyl ammonium chloride is most preferred. Other suitable cationic tensides as contemplated herein are quaternary protein hydrolysates. Alkylamidoamines are usually produced through the amidation of natural or synthetic fatty acids and fatty acid molecules with dialkylaminoamines. As contemplated herein, Tegoamid® S 18 (stearamidopropyldimethylamine) is a suitable compound from this substance group. Esterquats are substances containing both at least one ester function and at least quaternary ammonium group as the structural element. Preferred esterquats are quaternated ester salts of fatty acids with triethanolamine, quaternated ester salts of fatty acids with diethanolalkyl amines and quaternated ester salts of fatty acids with 1,2-dihydroxypropyldialkylamines. Such products are sold under the trade names of Stepantex, Dehyquart and Armocare.

With respect to optimum application properties and optimum dye results, C10-C22 alkyl trimethyl ammonium chloride has proved to be particularly suitable. Particularly preferred oxidant preparations used as contemplated herein (M2) are therefore exemplified in that they contain at least one cation tenside in a total quantity from about 0.05-about 3 wt. %, more preferably from about 0.1-about 1.5 wt. %, most preferably from about 0.3 to about 0.9 wt. %, in each case relative to the weight of the oxidant preparation (M2), wherein preferably at least one tenside, selected from C10-C22 alkyl trimethyl ammonium chlorides, most preferably selected from behenyl trimethyl ammonium chloride, stearyl trimethyl ammonium chloride and cetyl trimethyl ammonium chloride, as well as mixtures of said tensides, is contained. Oxidant preparations most preferred as contemplated herein (M2) contain stearyltrimethylammoniumchloride in a total quantity from about 0.05-about 3 wt. %, preferably from about 0.1-about 1.5 wt. %, more preferably from about 0.3-about 0.9 wt. %, in each case relative to the weight of the oxidant preparation (M2).

A further kit-of-parts preferred as contemplated herein is exemplified in that the oxidant preparation (M2) contains at least one cation tenside, preferably in a total quantity of from about 0.05-about 3 wt. %, more preferably from about 0.1-about 1.5 wt. %, most preferably from about 0.3-about 0.9 wt. %, in each case relative to the weight of the oxidant preparation (M2), but contains no polymer with a polymerization degree of at least about 200 and no polymer with a molecular weight of about 10,000 Dalton or higher.

It has emerged that the thickening aided by the interaction between the copolymer in the agent as contemplated herein and the cation tenside in the oxidant preparation (M2) is adequate, and due to the presence of a polymer with a polymerization degree of at least about 200 or a polymer with a molecular weight of about 10,000 Dalton or higher, is unable to further increase and/or even be adversely affected in terms of its application properties.

A further kit-of-parts preferred as contemplated herein is exemplified in that the oxidant preparation (M2) contains at least one cation tenside, which is preferably selected from stearyltrimethyl ammonium chloride, preferably in a total quantity of from about 0.05-about 3 wt. %, more preferably from about 0.1-about 1.5 wt. %, most preferably from about 0.3-about 0.9 wt. %, in each case relative to the weight of the oxidant preparation (M2), but contains no polymer with a polymerization degree of at least about 200 and no polymer with a molecular weight of about 10,000 Dalton or higher.

A method for oxidative hair dyeing as contemplated herein is exemplified in that the oxidant preparation (M2) contains at least one cation tenside, preferably in a total quantity of from about 0.05-about 3 wt. %, more preferably from about 0.1-about 1.5 wt. %, most preferably from about 0.3-about 0.9 wt. %, in each case relative to the weight of the oxidant preparation (M2), but contains no polymer with a polymerization degree of at least about 200 and no polymer with a molecular weight of about 10,000 Dalton or higher.

A further method for oxidative hair dyeing as contemplated herein is exemplified in that the oxidant preparation (M2) contains at least one cation tenside, which is preferably selected from stearyltrimethyl ammonium chloride, preferably in a total quantity of from about 0.05-about 3 wt. %, more preferably from about 0.1-about 1.5 wt. %, most preferably from about 0.3-about 0.9 wt. %, in each case relative to the weight of the oxidant preparation (M2), but contains no polymer with a polymerization degree of at least about 200 and no polymer with a molecular weight of about 10,000 Dalton or higher.

It has unexpectedly emerged that an application mixture having a viscosity particularly suitable for bottle application is obtained if the agent as contemplated herein or preferred as contemplated herein (M1) is mixed with an oxidant preparation (M2) containing at least one copolymer, selected from cross-linked acrylic acid/acrylic acid-C1-C6-alkyl ester copolymers and cross-linked methacrylic acid/acrylic acid-C1-C6-alkyl ester copolymers, preferably in a total quantity from about 0.1-about 7 wt. %, more preferably from about 0.5-about 6 wt. %, most preferably from about 1-about 4.5 wt. %, in each case relative to the weight of the oxidant preparation (M2). The mixing of the agent as contemplated herein or preferred as contemplated herein with such an oxidation preparation (M2) leads to the desired viscosity increase. The medium-viscosity consistency of the application mixture thus obtained leads to optimum application properties, more particularly for the bottle application. The application mixtures thus achieved, preferably with weight-based mixture ratios (M1):(M2) in the range of from about 1:0.8 to about 1:2.5 preferably have a viscosity in the range of from about 2000-about 50,000 mPas, more preferably from about 5000-about 40,000 mPas, even more preferably from about 8,000-about 30,000 mPas, most preferably from about 11,000-about 24,000 mPas, in each case measured at 20° C. (Brookfield viscometer, at a rotational frequency of 4 rpm with Spindle No. 5).

A further kit-of-parts preferred as contemplated herein is exemplified in that the oxidant preparation (M2) contains at least one copolymer, selected from cross-linked acrylic acid/acrylic acid-C1-C6 alkyl ester-copolymers and cross-linked methacrylic acid/acrylic acid-C1-C6-alkyl ester copolymers, preferably in a total quantity of from about 0.1-about 7 wt. %, more preferably from about 0.5-about 6 wt. %, most preferably from about 1-about 4.5 wt. %, in each case relative to the weight of the oxidant preparation (M2), and preferably contains no cation tenside.

A further method for oxidative hair dyeing as contemplated herein is exemplified in that the oxidant preparation (M2) contains at least one copolymer, selected from cross-linked acrylic acid/acrylic acid-C1-C6 alkyl ester-copolymers and cross-linked methacrylic acid/acrylic acid-C1-C6-alkyl ester copolymers, preferably in a total quantity of from about 0.1-about 7 wt. %, more preferably from about 0.5-about 6 wt. %, most preferably from about 1-about 4.5 wt. %, in each case relative to the weight of the oxidant preparation (M2), and preferably contains no cation tenside.

Preferred cross-linked copolymers of this type are selected from—in each case cross-linked—methacrylic acid/methylacrylate-, methacrylic acid/ethylacrylate-, methacrylic acid/propylacrylate-, methacrylic acid/butylacrylate-, methacrylic acid/pentylacrylate-, methacrylic acid/hexylacrylate-, acrylic acid/methylacrylate-, acrylic acid/ethylacrylate-, acrylic acid/propylacrylate-, acrylic acid/butylacrylate-, acrylic acid/pentylacrylate- and acrylic acid/hexylacrylate copolymers and the mixtures thereof.

A further kit-of-parts preferred as contemplated herein is exemplified in that the oxidant preparation (M2) contains at least one cross-linked copolymer, selected from—in each case cross-linked—methacrylic acid/methylacrylate-, methacrylic acid/ethylacrylate-, methacrylic acid/propylacrylate-, methacrylic acid/butyl acrylate-, methacrylic acid/pentylacrylate-, methacrylic acid/hexylacrylate-, acrylic acid/methyl acrylate-, acrylic acid/ethyl acrylate-, acrylic acid/propylacrylate-, acrylic acid/butylacrylate, acrylic acid/pentyl acrylate- and acrylic acid/hexylacrylate-copolymers and mixtures thereof, in a total quantity from about 0.1-about 7 wt. %, preferably from about 0.5-about 6 wt. %, most preferably from about 1-about 4.5 wt. %, in each case relative to the weight of the oxidant preparation (M2), and no cation tenside.

A further method preferred as contemplated herein is exemplified in that the oxidant preparation (M2) contains at least one cross-linked copolymer, selected from—in each case cross-linked—methacrylic acid/methylatate-, methacrylic acid/ethylacrylate-, methacrylic acid/propylacrylate-, methacrylic acid/butyl acrylate-, methacrylic acid/pentylacrylate-, methacrylic acid/hexylacrylate-, acrylic acid/methyl acrylate-, acrylic acid/ethyl acrylate-, acrylic acid/propylacrylate-, acrylic acid/butylacrylate, acrylic acid/pentyl acrylate- and acrylic acid/hexylacrylate-copolymers and mixtures thereof, in a total quantity from about 0.1-about 7 wt. %, preferably from about 0.5-about 6 wt. %, most preferably from about 1-about 4.5 wt. %, in each case relative to the weight of the oxidant preparation (M2), and no cation tenside.

Moreover, the oxidant preparations as contemplated herein and preferred as contemplated herein (M2) can contain stabilizers, more particularly complexing agents, and pH buffer substances.

With respect to the cosmetic agent (M1) in container C1 and the oxidant preparation (M2) in container C2 of the kit as contemplated herein and preferred as contemplated herein, the statements made about the agents as contemplated herein and preferred as contemplated herein apply mutatis mutandis.

With respect to the cosmetic agent (M1) in container C1 and the method for oxidative hair dyeing as contemplated herein and preferred as contemplated herein, the statements made about the agents as contemplated herein and preferred as contemplated herein apply mutatis mutandis.

With respect to oxidant preparation (M2) in container C1 and the method for oxidative hair dyeing as contemplated herein and preferred as contemplated herein, the statements made about the oxidant preparations (M2) of the kits as contemplated herein and preferred as contemplated herein apply mutatis mutandis.

EXAMPLES

The following examples are intended to explain the subject matter of the present disclosure without having any limiting effect.

TABLE 1

Dye gel for oxidative hair dyeing

| Ingredient | Test sample (wt. %) |
| --- | --- |
| Monoethanolamine (2-aminoethan-1-ol) | 5.00 |
| 1,2-Propanediol | 2.00 |
| Acrylates/C10-30 Alkyl Acrylate Crosspolymer | 0.70 |
| Xanthan gum | 0.10 |
| PEG-60 Hydrogenated Castor Oil | 2.00 |
| Perfume | 0.15 |
| Sodium sulfate | 0.40 |
| Etidronic acid | 0.06 |
| Toluen-2,5-diaminsulfate | 1.09 |
| Resorcin | 0.31 |
| 4-chlororesorcin | 0.25 |
| m-aminophenol | 0.04 |
| HC Yellow No. 13 | 0.03 |
| 2-amino-6-chlor-4-nitrophenol | 0.01 |
| Water | ad 100.00 |

Viscosity: 800 mPas (measured at 20° C. by employing a rotational viscometer at a rotational frequency of 20 rpm with Spindle 2)

TABLE 2

Dye gel for oxidative hair dyeing

| Ingredient | Test sample (wt. %) |
| --- | --- |
| Monoethanolamine (2-aminoethan-1-ol) | 5.00 |
| 1,2-Propanediol | 2.00 |
| Acrylates/C10-30 Alkyl Acrylate Crosspolymer | 0.70 |
| Xanthan gum | 0.10 |

TABLE 2-continued

Dye gel for oxidative hair dyeing

| Ingredient | Test sample (wt. %) |
|---|---|
| PEG-60 Hydrogenated Castor Oil | 2.00 |
| Perfume | 0.15 |
| Polyquaternium-7 | 0.12 |
| Sodium sulfate | 0.40 |
| Etidronic acid | 0.06 |
| Toluen-2,5-diaminsulfate | 1.09 |
| Resorcin | 0.31 |
| 4-chlororesorcin | 0.25 |
| m-aminophenol | 0.04 |
| HC Yellow No. 13 | 0.03 |
| 2-amino-6-chlor-4-nitrophenol | 0.01 |
| Water | ad 100.00 |

TABLE 3

Developers containing oxidant for the color gels from Table 1 and Table 2

| Ingredient | Test sample (wt. %) |
|---|---|
| Sodium benzoate | 0.04 |
| Dipicolinic acid (2,6-dicarboxypyridin) | 0.10 |
| Di-sodium pyrophosphate | 0.10 |
| Potassium hydroxide | 0.10 |
| 1,2-Propanediol | 1.00 |
| Etidronic acid | 0.15 |
| Paraffin oil | 0.30 |
| Stearyl trimethyl ammonium chloride | 0.30 |
| Cetearyl alcohol | 340 |
| Ceteareth-20 | 1.00 |
| Hydrogen peroxide | 6.00 |
| Water | ad 100.00 |

Viscosity: 4,500 mPas, measured at 20° C. with a rotational viscometer Haake VT 550 at a rotational frequency of 4 rpm with measurement geometry MV II

TABLE 4

Developers containing oxidant for the color gels from Table 1 and Table 2

| Ingredient | Test sample (wt. %) |
|---|---|
| Sodium hydroxide | 0.40 |
| Dipicolinic acid (2,6-dicarboxypyridin) | 0.10 |
| Di-sodium pyrophosphate | 0.03 |
| Etidronic acid | 0.15 |
| Mixture of cross-linked (meth)acrylic acid/acrylic acid-C1—C6-alkyl ester copolymers (ex Aculyn 33A) | 4.20 (Active) |
| Sodium laureth(2)sulfate | 0.50 |
| Hydrogen peroxide | 6.00 |
| Water | ad 100.00 |

* Aculyn 33A: hydrous dispersion of Acrylates Copolymer (mixture of cross-linked (meth)acrylic acid/acrylic acid-C1-C6-alkyl ester copolymers); 28 wt. % polymer content (active substance)
Viscosity: * Viscosity: measured at 20° C. by employing a Brookfield rotational viscometer at a rotational frequency of 20 rpm with Spindle 2

Production of the Application Mixtures and Coloration on Hair

Dye gel and developer according to Table 5 were mixed with one another in a homogeneous manner. The application mixtures thus obtained were applied, immediately after production, to human hair (natural white hair, Kerling) (liquor ratio 4 gram application mixture per gram of hair and left on the hair for 30 minutes at room temperature (22° C.). The strands were then rinsed out and towel-dried.

TABLE 5

Production of the application mixtures for coloration on hair

| Dye gel (M1) (agent as contemplated herein) | Developer (M2) | Weight ratio (M1):(M2) | Viscosity of the application mixture [mPas]* |
|---|---|---|---|
| according to Table 1 | according to Table 3 | 1:2 | 26,000 |
| according to Table 1 | according to Table 3 | 1:1 | 31,000 |
| according to Table 1 | according to Table 4 | 1:2 | 15,000 |
| according to Table 1 | according to Table 4 | 1:1 | 13,000 |
| according to Table 2 | according to Table 3 | 1:2 | 56,000 |
| according to Table 2 | according to Table 3 | 1:1 | 47,000 |
| according to Table 2 | according to Table 4 | 1:2 | 23,000 |
| according to Table 2 | according to Table 4 | 1:1 | 22,000 |

*Viscosity: measured at 20° C. by employing a Brookfield rotational viscometer at a rotational frequency of 4 rpm with Spindle 5.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. Agent for oxidative hair dyeing comprising, relative to the weight of the agent,
    from about 78-about 95 wt. %, water,
    at least one oxidation dye precursor,
    at least one alkalizing agent,
    at least one non-ionic tenside in a total quantity of from about 0.1-about 3 wt. %,
    at least one cross-linked copolymer composed of acrylic acid and non-ethoxylated esters of acrylic acid with linear C10-C30 monoalcohols as monomers, wherein the cross-linked copolymer is present in a total quantity of from about 0.05 to about 2 wt. %,
    from about 0.001-about 0.5 wt. % xanthan gum,
    at least one linear, saturated alkanol with two or three hydroxy groups and from about 2 to about 8 carbon atoms in the alkyl group in a total quantity of from about 0-about 3 wt. %,
    wherein
    no saturated or unsaturated non-alkoxylated alkanols with a hydroxy group and from about 1 to about 50 carbon atoms in the alk(en)yl group and
    no saturated or unsaturated alkanecarboxylic acids with from about 1 to about 50 carbon atoms, and
    no oxidants
    are included in the agent.

2. Agent according to claim 1, wherein the alkalizing agent is selected from the group comprising ammonium hydroxide, basic amino acids, alkalihydroxides, alkanolamines, alkali metal metasilicates, alkali phosphates, alkali hydrogen phosphates, or mixtures thereof.

3. Agent according to claim 1, wherein the at least one non-ionic tenside is selected from ethoxylated castor oil having from about 7-about 80 mol ethylene oxide per mol.

4. Agent according to claim 1, wherein the agent comprises sodium polyacrylate.

5. Agent according to claim 1, having a viscosity in the range of from about 10-about 2000 mPas, measured at 20° C. by employing a Brookfield rotational viscometer at a rotational frequency of 20 rpm with Spindle 2.

6. Agent according to claim 1, having a pH value in the range of from about 8-about 12, measured at 20° C.

7. Agent according to claim 1, wherein the agent comprises sodium polyacrylate having a mass-average molar mass $M_w$ in the range from about 1,000,000 to about 20,000,000 Dalton.

8. Agent according to claim 7, having a viscosity in the range of from about 10,000-about 75,000 mPas, measured at 20° C. by employing a Brookfield rotational viscometer at a rotational frequency of 4 rpm with Spindle 5.

9. Kit-of-parts comprising—packaged separately from one another—
   a) at least one container (C1), comprising an agent for oxidative hair dyeing according claim 1, and
   b) at least one container (C2), comprising an oxidant preparation (M2), which comprises from about 40-about 96 wt. % of water, and which has a pH value in the range from about 2.0 to about 6.5, measured at 20° C., wherein each of the wt. % values are relative to the weight of the oxidant preparation (M2).

10. Kit-of-parts according to claim 9, wherein the oxidant preparation (M2) comprises at least one cation tenside.

11. Kit-of-parts according to claim 10, wherein the oxidant preparation (M2) comprises no polymer with a polymerization degree of at least about 200 and no polymer with a molecular weight of about 10000 Dalton or higher.

12. Kit-of-parts according to claim 9, wherein the oxidant preparation (M2) comprises at least one copolymer selected from cross-linked acrylic acid/acrylic acid-C1-C6 alkyl ester-copolymers and cross-linked methacrylic acid/acrylic acid-C1-C6-alkyl ester copolymers, and contains no cation tenside.

13. Method for oxidative hair dyeing, comprising the following method steps:
   i) Providing a cosmetic agent (M1) for oxidative hair dyeing according to claim 1,
   ii) Providing an oxidant preparation (M2), which comprises from about 40-about 96 wt. % of water, also hydrogen peroxide in a total quantity of from about 0.5 to about 23 wt. %, and which has a pH value in the range from about 2.0 to about 6.5, measured at 20° C., wherein each of the wt. % values are relative to the weight of the oxidant preparation (M2), wherein optionally, either at least one cation tenside or at least one copolymer, selected from cross-linked acrylic acid/acrylic acid-C1-C6-alkyl ester-copolymers and cross-linked methacrylic acid/acrylic acid-C1-C6-alkyl ester-copolymers is included,
   iii) Mixing the cosmetic agent (M1) with the oxidant preparation (M2), immediately afterwards,
   iv) Applying the mixture obtained in Step iii) onto the hair and leaving said mixture for a period of from about 1 to about 60 minutes, at room temperature or at from about 30-about 60° C. on the hair,
   v) Rinsing the hair with water and/or a cleansing composition, and
   vi) where necessary, applying a post-treatment agent onto the hair and, where necessary, rinsing out, then drying.

14. Method for oxidative hair dyeing according to claim 13, wherein the oxidant preparation (M2) comprises at least one cation tenside, and comprises no polymer with a polymerization degree of at least about 200 and no polymer with a molecular weight of about 10000 Dalton or higher.

15. Method for oxidative hair dyeing according to claim 13, wherein the oxidant preparation (M2) comprises at least one copolymer, selected from cross-linked acrylic acid/acrylic acid-C1-C6 alkyl ester-copolymers and cross-linked methacrylic acid/acrylic acid-C1-C6-alkyl ester copolymers, and comprises no cation tenside.

16. Agent according to claim 1, wherein the at least one non-ionic tenside is selected from ethoxylated castor oil having from about 40-about 55 mol ethylene oxide per mol.

17. Agent according to claim 1, having a pH value in the range of from 9.5-10.5, measured at 20° C.

18. Agent according to claim 7, wherein the sodium polyacrylate is present in a total quantity of from about 0.1-about 1.5 wt. %, relative to weight of the agent.

19. Kit-of-parts according to claim 10, wherein the at least one cation tenside is present in a total quantity of from about 0.05-about 3 wt. %, relative to the weight of the oxidant preparation (M2).

20. Agent according to claim 1, wherein:
   the water is present in an amount of from about 83-about 91 wt. %,
   the at least one non-ionic tenside is selected from ethoxylated castor oil having from about 7-about 80 mol ethylene oxide per mol and is present in a total quantity of from about 0.8-about 2 wt.-%,
   the xanthan gum is present in an amount of from about 0.05-0.1 wt. %, and
   the agent has a pH value in the range of from about 8-about 12, measured at 20° C.,
   wherein all amounts are relative to weight of the agent.

* * * * *